US008906832B2

(12) United States Patent
Wong et al.

(10) Patent No.: US 8,906,832 B2
(45) Date of Patent: Dec. 9, 2014

(54) QUANTITATIVE ANALYSIS OF CARBOHYDRATE-PROTEIN INTERACTIONS USING GLYCAN MICROARRAYS: DETERMINATION OF SURFACE AND SOLUTION DISSOCIATION CONSTANTS

(75) Inventors: Chi-Huey Wong, La Jolla, CA (US); Pi-Hui Liang, Taipei (TW)

(73) Assignee: Academia Sinica, Nangkang, Taipei (TW)

(*) Notice: Subject to any disclaimer, the term of this patent is extended or adjusted under 35 U.S.C. 154(b) by 602 days.

(21) Appl. No.: 12/423,733

(22) Filed: Apr. 14, 2009

(65) Prior Publication Data

US 2009/0275484 A1 Nov. 5, 2009

Related U.S. Application Data

(60) Provisional application No. 61/049,358, filed on Apr. 30, 2008.

(51) Int. Cl.

| | |
|---|---|
| ***C07H 3/00*** | (2006.01) |
| ***C40B 40/12*** | (2006.01) |
| ***B01J 19/00*** | (2006.01) |
| ***C40B 30/04*** | (2006.01) |
| *C40B 20/02* | (2006.01) |

(52) U.S. Cl.

CPC ............. *C40B 30/04* (2013.01); *B01J 19/0046* (2013.01); *G01N 2400/10* (2013.01); *C40B 40/12* (2013.01)

USPC ...... 506/19; 506/3; 506/39; 536/2; 536/123.1

(58) Field of Classification Search

CPC ........... C08B 37/0003; G01N 2400/00; G01N 2400/10; C07H 3/00; B01J 19/0046; C40B 40/12

USPC ............................ 506/3, 19, 39; 536/2, 123.1

See application file for complete search history.

(56) References Cited

PUBLICATIONS

Liang et al., "Quantitative Analysis of Carbohydrate-Protein Interactions Using Glycan Microarrays: Determination of Surface and Solution Dissociation Constants", 2007, JACS, 129:11177-84.*

Park et al., "Carbohydrate Microarrays for Assaying Galactosyltransferase Activity", 2007,Organic Letters, 9(9):1675-8.*

Angeloni et al., "Glycoprofiling with Micro-arrays of Glycoconjugates and Lectins", 2005, Glycobiology, 15(1):31-41.*

Feizi et al., Curr. Opin. Struct. Biol., 2003, 13:637-645.*

Gupta et al. (Biochemistry, 1994, 33:5526-5530).*

Alvarez, R.; Blixt, O. Methods Enzymol. 2006, 415, 292-310.

Mandel D. K.; Kishore, N.; Brewer, C. F. Biochemistry 1994, 33, 1149-1156.

Park, S.; Shin, I. Org. Lett. 2007, 9, 1675-1678.

(Continued)

*Primary Examiner* — Christopher M Babic

*Assistant Examiner* — Jeremy C Flinders

(74) *Attorney, Agent, or Firm* — Eckman Basu LLP

(57) ABSTRACT

A method, system and device to identify, study and/or mimic carbohydrate-protein interactions on cell surfaces and in solution measured by a glycan microarray. In some instances the method, system and device uses very small quantities of carbohydrate as low as attomol. In some instances the system, method and device is high-throughput. The small quantity sensitivity may allow for close placement of carbohydrate array members wherein due to close proximity multivalent interactions with proteins may be identified.

3 Claims, 20 Drawing Sheets

OSu
OSu
Man1
FITC-Con A
1fM
1 nM (s/n ≥10)
100 mM

(56) References Cited

PUBLICATIONS

Gordus, A.; MacBeath, G. J. Am. Chem. Soc. 2006, 128, 13668-13669.
Kce ller, K. M.; Wong, C. -H. Nat. Biotech. 2000, 18, 835-841.
Berto zzi, C. R.; Kiessling, L. L. Science 2001, 291, 2357-2364.
Dube, D. H.; Bertozzi, C. R. Nat. Rev. Drug Disc. 2005, 4, 477-488.
W eis, W. I.; Drickamer, K. Annu. Rev. Biochem. 1996, 65, 441-473.
Lee Y. C.; Lee. R. Acc. Chem. Res. 1995, 28, 321-327.
Kiessl ing, L. L.; Pohl, N. L. Chem. Biol. 1996, 3, 71-77.
Do yle, M. L. Curr. Opin. Biotechnol. 1997, 8, 31-35.
Heeg aard, N. H. H.; Nilsson, S.; Guzman, N.A. J. Chromatogr. B, 1998, 715, 29-54.
Mann , D. A.; Kanai, M.; Maly, D. J.; Kiessling, L. L. J. Am. Chem. Soc. 1998, 120, 10575-10582.
Hirab ayashi, J.; Arata, Y.; Kasai, K. J. Chromatogr. A 2000, 890, 261-271.
Houseman, B. T.; Mrksich, M. Ch em. Biol. 2002, 9, 443-454.
Bl ixt, O., et al.; Cummings, R. Bovin, N.; Wong, C.-H.; Paulson, J. C. Proc. Natl. Acad. Sci. USA 2004, 101, 17033-17038.
Huan g, C.-Y.; Thayer, D. A.; Chang, A.Y.; Best, M. D.; Hoffmann, J.; Head, S.; Wong, C. -H. Proc. Natl. Acad. Sci. USA 2006, 103, 15-20.
Pat wa, T. H.; Zhao, J.; Anderson, M. A.; Simeone, D, M; Lubman, D. M. Anal. Chem. 2006, 78, 6411-6421.
Br yan, M. C; Fazio, F.; Lee, H.-K.; Huang, C.-Y.; Chang, A.; Best, M. D.; Calarese, D. A.; Blixt, O.; Paulson, J. C.; Burton, D.; Wilson, I. A.; Wong, C. -H. J. Am. Chem. Soc. 2004, 126, 8640-8641.
Ko, K. S.; Jaipuri., F. A.; Pohl, N. L. J. Am Chem. Soc. 2005, 127, 13162-13163.
Park. S.; Le e, M. R.; Pyo, S. J.; Shin, I. J. Am. Chem. Soc. 2004, 126, 4812-4819.
Park, S.; S hin, I. Angew. Chem. Int. Ed. 2002, 41, 3180-3182.
Ratner, D. M.; Adams, E. W.; Disney, M. D.; Seeberger, P. H. ChemiBioChem 2004, 5, 1375-1383.
Xia, B.; Kawar, Z. S.; Ju. T.; Alvarez, R.; A; Sachdev, G. P.; Cummings, R. D. Nat. Methods 2005 , 2, 845-850.
Bradn er, J. E.; McPherson, O. M.; Mazitschek, R.; Barnes-Seeman, D.; Shen, J. P.; Dhaliwal, J.; Stevenson, K. E.; Duffner, J. L.; Park, S. B.; Neuberg, D. S.; Nghiem, P.; Schreiber, S. L.; Koehler, A. N. Chem. Biol. 2006, 13, 493-504.
Jones, R. B.; Gordus, A.; Krall, J. A; MacBeath, G. Nature 2006, 439, 168-174.
Haes, A . J.; Van Duyne, R. P. J. Am. Chem. Soc. 2002, 124, 10596-10604.
Smith, E. A.; Thomas, W. D.; Kiessling, L. L.; Corn, R. M. J. Am. Chem. Soc., 2003, 125, 6140-6148.
W egner, G. J.; Lee, H. J.; Corn, R. M. Anal. Chem. 2002, 74, 5161-5168.
Horan, N .; Yan, L.; Isobe, H.; Whitesides, G. M.; Kahne, D. Proc. Natl. Acad. Sci. USA 1999, 96, 11782-11786.
Kiessl ing L. L.; Gestwicki, J. E.; Strong, L. E. Angew. Chem. Int. Ed. 2006, 45, 2348-2368.
Kitov P. I.; Sadowska, J. M.; Mulvey, G.; Armstrong, G. D.; Ling, H.; Pannu, N. S.; Read, R. J.; Bun dle, D. R. Nature 2000, 403, 669-672.
Mam men, M.; Choi, S. K.; Whitesides, G, M. Angew. Chem. Int. Ed. 1998, 37, 2754-2794.
Leek, H.-K.; Scanlan, C. N.; Huang, C.-Y.; Chang, A. Y.; Calarese, D. A.; Dwek, R. A.; Rudd, P. M.; Burton, D. R.; Wilson, I. A.; Wong, C.-H. Angew. Chem. Int. Ed. 2004, 43, 1000-1003.
Calar ese, D. A.; Lee, H.-K.; Huang, C.-Y.; Best, M. D.; Astronomo, R. D.; Stanfield, R. L.; Katinger, H.; Burton, D. R.; Wong, C.-H.; Wilson, I. A. Proc. Natl: Acad. Sci. USA 2005, 102, 13372-13377.
Deeds, E. J.; Ashenberg, O.; Shakhnovich, E. I. Proc. Natl. Acad. Sci. USA 2006, 103, 311-316.
Gutiérr ez Gallego, R.; Haseley, S. R.; van Miegem, V. F.; Vliegenthart, J. F.; Kamerling, J. P. Glycobiology 2004, 12, 373-386.
Dam, T. K.; Oscarson, S.; Sacchettini, J. C.; Brewer, C. F. J. Biol. Chem. 1998, 273, 32826-32832.
Scott, J. K.; Loganathan, D.; Easley, R. B.; Gong, X.; Goldstein, I. J. Proc. Natl. Acad. Sci. U.S.A. 1992, 89, 5398-5402.
Atti e, A. D.; Raines, R. T. J. Chem. Ed. 1995, 72, 119-124.

* cited by examiner

Man4

Man4

Man8

LCA

Man9

PSA

Man1

PSA

Man4

PSA

Man8

PSA

Man9

2G12

Man1

2G12

Man4

2G12

Man8

Man9

Fig. 9

| Printing Conc. mM | $F_{max}$ | $K_{D,surf,}$ nM |
|---|---|---|
| 100 | 40950 | 80.4 |
| 80 | 40030 | 76.8 |
| 40 | 34050 | 81.7 |
| 30 | 29490 | 88.7 |
| 20 | 26910 | 90.6 |
| 10 | 22670 | 81.8 |
| 1 | 18250 | 221 |
| 0.6 | 14250 | 214 |

Fig. 10

| Competitors | Array (mM) | ITC (mM) | SPR (mM) |
|---|---|---|---|
| a-MeMan | 0.16 | 0.12 | 0.09 |
| a-MeGlc | 0.69 | 0.52 | 0.29 |
| a-MeGal | -[a] | - | - |
| Mannose | 1.2 | - | - |
| Glucose | 25 | - | - |
| Galactose | 80 | - | - |

[a] 20% inhibition at 100 mM. "-" not determined.

QUANTITATIVE ANALYSIS OF CARBOHYDRATE-PROTEIN INTERACTIONS USING GLYCAN MICROARRAYS: DETERMINATION OF SURFACE AND SOLUTION DISSOCIATION CONSTANTS

RELATED APPLICATIONS

This application claims the benefit of and priority to U.S. Provisional Application Ser. No. 61/049,358, filed Apr. 30, 2008, the contents of which are incorporated by reference herein in its entirety.

FIELD OF DISCLOSURE

This disclosure relates to sensitive, high throughput, glycan microarray systems, methods and devices for examining carbohydrate-protein interactions on surface and in solution. More particularly, the glycan microarray is a platform for using very small amounts of materials. The glycan microarray supports multivalent interactions and may be used to determine the surface dissociation constant ($K_{D,\ surf}$).

BACKGROUND

Carbohydrates can be envisioned as the K'nex™ toys of life. They are building blocks with multiple points of attachment, which can form highly branched and stereochemically-rich structures. They are difficult to study because the connecting points are not as sturdy as the K'nex. In fact, the binding force is very weak compared to the binding force of an antigen or antibody. The affinities, i.e., the force of attraction between molecules, of the latter can be $10^3$-$10^9$ greater. Therefore, it is very difficult to synthesize a sufficient quantity of a carbohydrate for lab analysis. Traditionally it may take a day or more to measure a single carbohydrate-protein interaction using compounds in microgram to milligram amounts.

Carbohydrates, present as free oligosaccharides or as glycoconjugates, play an important role in many biological events, particularly those involving cell surfaces. Specific interactions between carbohydrates and proteins are often essential in viral and bacterial infection, the immune response, differentiation and development, and the progression of tumor cell metastasis. Therefore an understanding of carbohydrate-protein interactions at the molecular level would lead to a better insight into the biological process of living systems and assist the development of therapeutic and diagnostic strategies.

Despite the ubiquity and importance of carbohydrates in biology, difficulties in the study of carbohydrate-protein interactions have hindered the development of a mechanistic understanding of carbohydrate structure and function. The structural complexity of carbohydrates is a major obstacle: while the other two classes of biopolymers, nucleic acid and proteins, have a linear arrangement of repeating units, carbohydrate building blocks have multiple points of attachment, leading to highly branched and stereochemically-rich structures. In addition, binding affinities are weak typically in the ~$10^{-3}$-$10^{-6}$ M range of dissociation constants, compared with antigen-antibody interactions ($10^{-8}$-$10^{-12}$). While techniques such as isothermal titration calorimetry (ITC), affinity capillary electrophoresis, surface plasmon resonance (SPR), and frontal affinity chromatography are all significant advances, they are often limited by the amount of available materials.

Hence, the design of sensitive and high throughput technologies for characterizing carbohydrate-protein interactions remain a challenge.

However, little attention has been paid to the systematic kinetic and thermodynamic investigation of the interactions using glycan microarrays. Recently, MacBeath et al. reported a quantitative analysis of protein-peptide interactions using a protein microarray; in this work the interactions of Src homology 2 and the phosphotyrosine binding domain of phosphopeptides were measured, and this study provided a better understanding of the tyrosine phosphorylation network for the epidermal growth factor receptor.

SUMMARY

The Glycan microarray or "sugar-chip" disclosed herein is a platform for the investigation and manipulation of carbohydrate-protein interactions. Assessing carbohydrate affinities is typically difficult due to weak affinities and limited sources of structurally complex glycans. Disclosed herein is a sensitive glycan microarray technology for the simultaneous determination of a wide variety of parameters in a single experiment using small amounts of materials. In some aspects this microarray is also high throughput.

In some exemplary implementations, a dense carbohydrate microarray for quantitative protein measurements is disclosed. The microarray may comprise: a solid substrate configured to provide a supporting substance; and a reactive layer fabricated on the solid substrate, the reactive layer comprising at least one reactive group of small molecules; wherein the at least one reactive group of small molecules is configured to bind with at least one protein, wherein the at least one protein are immobilized on the solid substrate via the reactive layer; wherein the carbohydrate microarray is configured to perform a quantitative measurement of binding ability with the at least one protein; wherein at least three different concentrations of the at least one protein are provided in one chip; wherein the binding affinity between the small molecules and the at least one protein can be measured; wherein the small molecules comprise at least one of carbohydrates and glycolipids; wherein the small molecules are disposed relative to each other to allow the at least one protein to multivalently bond with the small molecules.

In some exemplary implementations, a kit is disclosed. The kit may comprise: a high throughput carbohydrate microarray comprising carbohydrate spots on a solid substrate, each of the carbohydrate spots having a reactive group of at least one of carbohydrates and glycolipids, wherein the carbohydrates spots are configured to react with and bind to at least one protein; wherein the reactive groups are disposed relative to each other to allow the at least one protein to multivalently bond with the reactive groups; a microarray reader; and instructions for use.

In some exemplary implementations, a method for identifying a protein bound to a microarray of attomol quantity carbohydrates is disclosed. The method may comprise: forming a glycan microarray of spotted sugars in concentrations each of about $10^{-18}$ mole; adding a labeled protein to the microarray; incubating the microarray; and, using an array reader to identify labeled proteins on the glycan microarray.

DRAWINGS

The above-mentioned features and objects of the present disclosure will become more apparent with reference to the following description taken in conjunction with the accompanying drawings wherein like reference numerals denote like elements and in which:

FIG. 1 shows an implementation of glycan microarray fabrication and detection. The N-hydroxysuccinimide (NHS) activated glass slide was printed with Man1 at a range of concentrations between 100 mM and 0.5 fM. Fluorescent images were then probed with FITC labeled Con A. The detection limit was determined to be at 1 nM printing concentration and atto-mol quantities of sugars per spot. Arrow refers to the printing concentration. The white bar (bottom right) equals 0.5 mm length. Limit of detection is signal to noise greater than 10 (s/n≥10). At this value, the sugar concentration per print is about 1 nM. Every print load is about 0.7 nL per spot. These small quantities (attomol) of samples are sufficient to meet the defined detection limits. (1 attomol is $10^{-18}$ mol of a molecule.)

FIG. 2 shows an implementation of (a) Mono-mannose cadaverine was printed with concentrations of 100 (first left column), 80, 60, 40, 30, 20, 10, 8, 6, 4, 2, 1, 0.8, 0.6, 0.4, and 0.1 μM (first right column) The images were obtained from slides incubated with different concentrations of FITC labeled Con A (from 800 nM to 25 nM as indicated above each square). (b) Binding curves for Man1 printed at different concentrations are shown. The curves were obtained using FITC labeled Con A. The $K_{D,\ surf}$ values were obtained by fitting the curves in panel A to eq 1.

Figure 6:
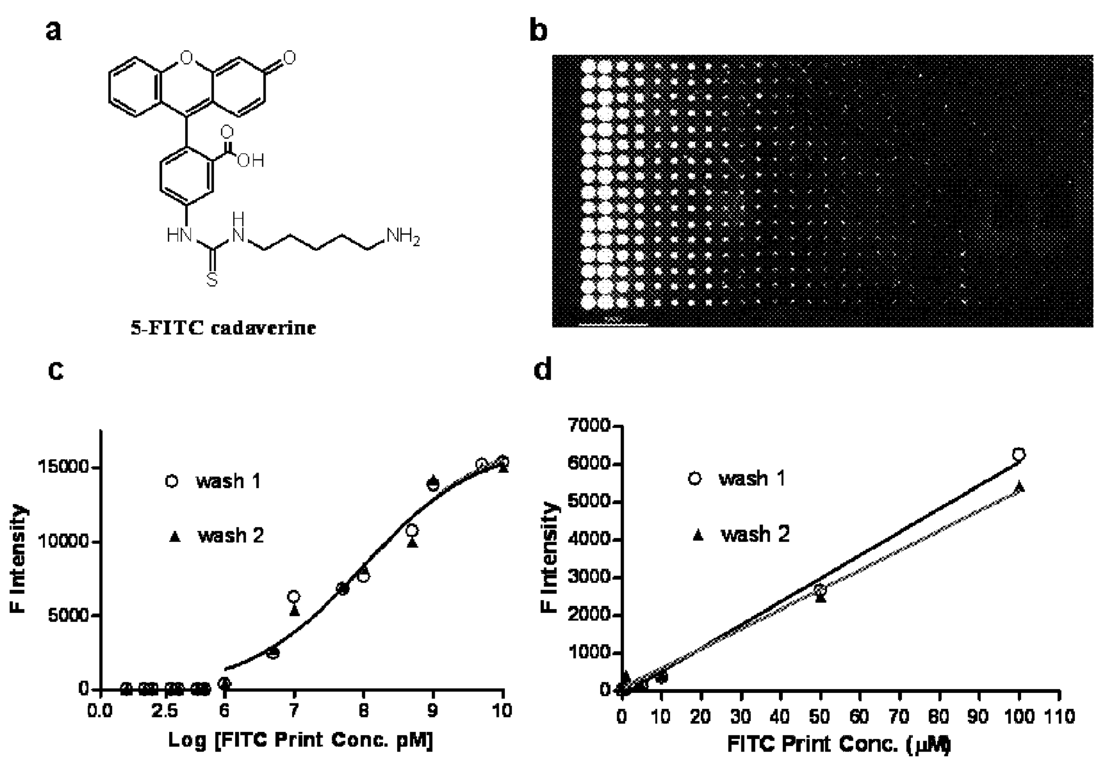

FIG. 6 shows implementations of (a) structure of FITC cadaverine. (b) FITC cadaverine was printed with different concentrations from 100 mM (first left column), 50 mM, 10 mM, 5 mM, 1 mM, 500 μM, 100 μM, 50 μM, 10 μM, 5 μM, 1 μM, 500 nM, 100 nM, 50 nM, 10 nM, 5 nM, 1 nM, 500 pM, 100 pM, 50 pM, 10 pM, 5 pM, 1 pM, 500 fM, 100 fM, 50 fM, 10 fM, 5 fM, 1 fM, 0.5 fM (first right column) The image was obtained by array reader after slide was washed with PBST (0.05% Tween 20). (c) The curves were obtained by the function of logarithm of printing conc. and median fluorescence intensities. Wash 1 and wash 2 are two independent experiments. (d) Replotted the function of the printing conc. (from 100 mM to 0.05 mM) and median fluorescence intensities. Goodness to fit: $R^2$>0.99 for both lines.

Figure 7A:
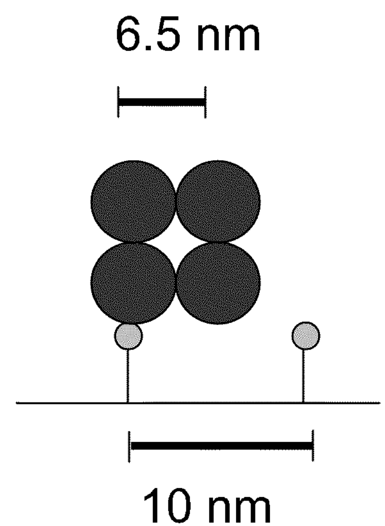
Figure 7B:
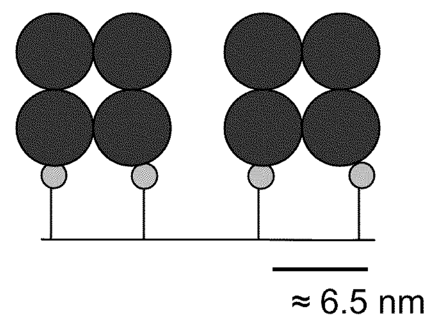

FIG. 7 illustrates implementations of sugar chips at different concentrations. Each dark group of four circles represents a protein. The large protein is shown interacting with the light array members. In FIG. 7*a* the array members are physically closer together; a protein may therefore interact multivalently as opposed to the situation in FIG. 7*b* wherein the physical gap between array members makes it difficult for a protein to interact with multiple array members at the same time.

Figure 8:
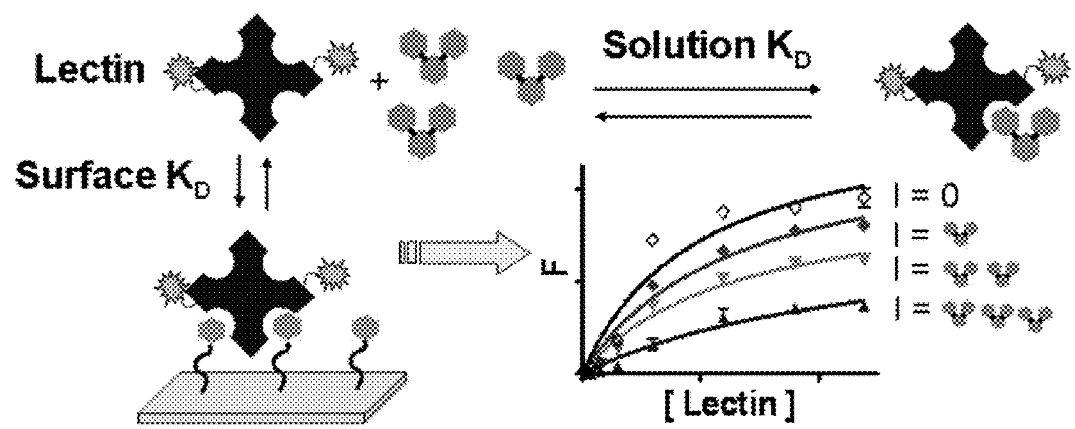

FIG. 8 is a diagrammatic overview of implementations of a sensitive glycan microarray. The sugar fixed to the surface of the substrate interacts with different concentrations of lectin (shown here which a florescence attached). To obtain the surface KD value different concentration of inhibitors (light grey connected hexagons) were added, each concentration of inhibitor will generate an isotherm (right bottom chart.). Based on the isotherms, the solution KD or Ki for the inhibitors may be obtained.

FIG. 9 shows a table providing data on the functions of different printing concentration, and the corresponding fluorescence intensities, and the dissociate constants on surface.

FIG. 10 shows a table providing data on competitors and solution Ki values for the interaction with Con A.

Figure 11:
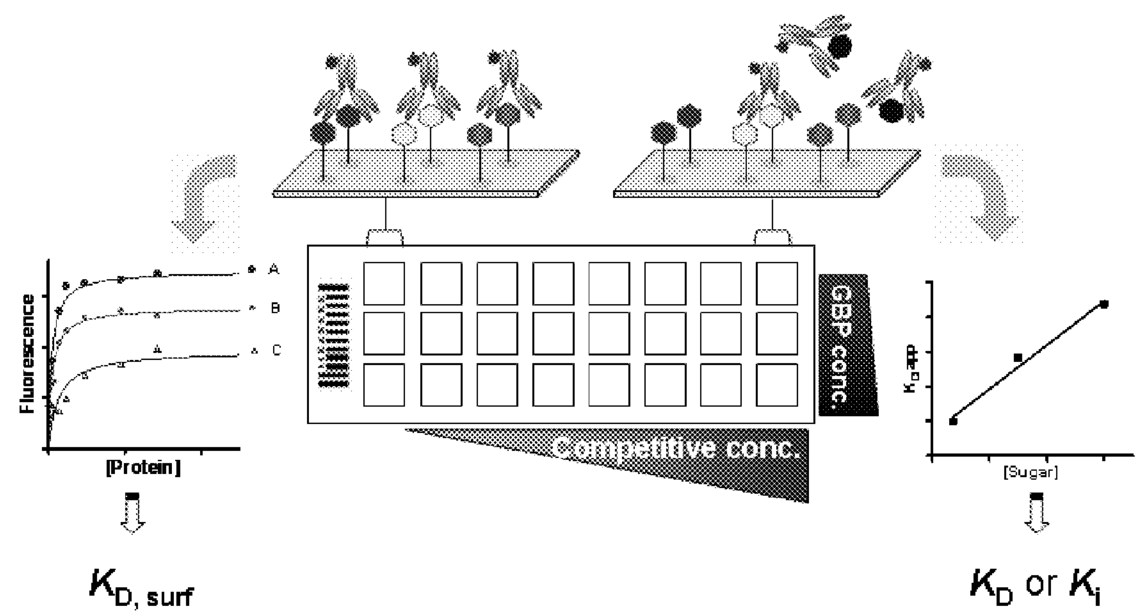

FIG. 11 shows implementations of quantitative analysis of protein-carbohydrate interactions to obtain surface and solution dissociation constants from glycan arrays. Carbohydrates with reactive groups are immobilized on the array surface. The device (one chip) contains 2 to 50 subarray (□), each subarray contains several carbohydrates. When the device are immobilized with one protein (carbohydrate binding protein) with several (at least 3) concentrations, it will generate an isotherm where the apparent dissociation constant ($K_{D,\ surf}$) can be obtained (left isotherm). In the same system, when a different concentrations of carbohydrate (sugar) is co-immobilized with protein. A new isotherm (right isotherm) derived from carbohydrate concentrations and apparent dissociation constants will give the solution dissociation ($K_i$ or $K_D$) of free carbohydrate.

DETAILED DESCRIPTION

In some exemplary implementations of the disclosure surface-based carbohydrate arrays is used to identify lectin recognition.

In some exemplary implementations of the disclosure the presentation of carbohydrates in a microarray provide a system and method to monitor multiple binding events and/or the effects of multivalency. In some instances implementations of the disclosure carbohydrate-protein interactions on cell surface and in solution can be quantitatively measured by glycan microarray.

In some exemplary implementations of the disclosure a glycan microarray with attomol-limits of detection (1 attomol is $10^{-18}$ mol of a molecule) is disclosed. Thus, about one milligram of a carbohydrate may be used for a large number of tests. In some instances a milligram of carbohydrate may be used as many as $10^{12}$ times. In some instances very slight amounts of antibodies in a subject's blood stream, which can not be detected, by any other known method may be detected.

In some exemplary implementations a method for the determination of sugar density using fluorescein isothiocyanate cadaverine to discover, confirm and/or solve the distance of two binding sites within one protein.

In some exemplary implementations a method to mimic cell surface carbohydrate-protein interactions of at least one of binding mode and strength of carbohydrate-protein interaction.

In some exemplary implementations a glycans array to mimic cell surface carbohydrate-protein interactions of at least one of binding mode and strength of carbohydrate-protein interaction which uses a very small amount of carbohydrate.

In some exemplary implementations a method is disclosed to characterize sugar binding specificities of proteins.

In some exemplary implementations a method is disclosed for high throughput identification of inhibitors of carbohydrate-binding proteins.

In some exemplary methods disclosed herein the apparent binding mode and strength of carbohydrate-protein interaction on cell surfaces are disclosed to be mimicked and can be quantitatively analyzed by glycan array in a rapid manner using only a very small amount of carbohydrate.

According to another aspect, one or more kits of parts can be envisioned by the person skilled in the art, the kits of parts to perform at least one of the methods herein disclosed, the kit of parts comprising one or more microarray devices, a solid substrate configured to provide a supporting substance; and a reactive layer fabricated on the solid substrate, the reactive layer comprising at least one reactive group of small molecules, according to implementations disclosed herein. The kits possibly include devices for reading, operating, interpreting, or processing data produced by the one or more microarrays, as well as instructions for use of the kit and its constituent parts. For example, a kit may include a microarray reader for analyzing a microarray after a reaction.

Arraying and Detection Limit.

A strategy for covalently attaching a defined glycan to a glass slide was based on the standard microarray robotic printing technology using N-hydroxysuccinimide (NHS) activated glass surface, to which glycans containing an amine linked to the anomeric position were covalently attached. Prior to producing the slides, the challenges of printing concentrations were examined. Because carbohydrates do not fluoresce and modified carbohydrates bearing fluorescent groups might interact differently with the protein, fluorescein isothiocyanate (FITC) cadaverine was used as a model.

Figure 1:
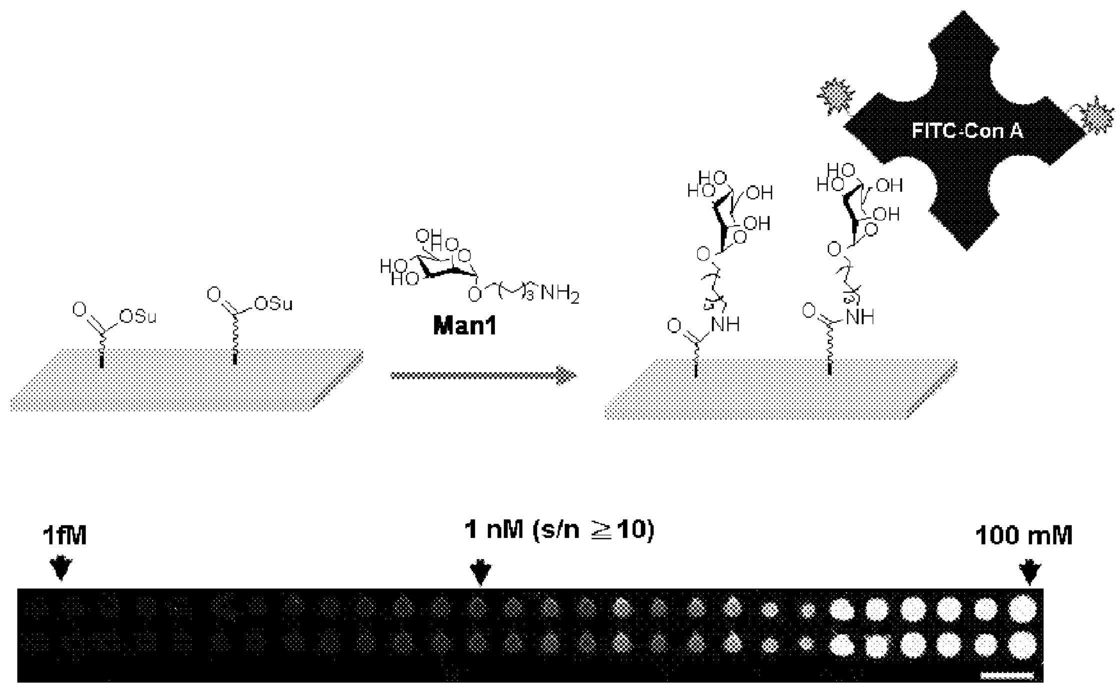

FITC cadaverine was printed in concentrations ranging from 100 mM to 1 fM and the slide was scanned before and after washing. The surface coverage of FITC was measured in a fluorescence wash-off experiment and the density of maximum loading was found to be $10^{14}$ molecules/cm$^2$ a similar value to most peptides or sugars attached to SPR biosensor surface. More importantly, at concentrations below 100 μM, the fraction of surface covered by each molecule varied in proportion to its concentration, while over 500 μM, the surface seemed to be saturated (FIGS. 6a-6d). Next, mono-mannose derivative bearing primary amine (Man1) were printed on the glass slide in concentrations ranging from 100 mM to 0.5 fM (FIG. 1) and incubated with FITC-labeled Con A (100 nM). The limit of detection was found to be in the nanomolar printing concentration, when the ratio of signal to noise was more than 10. This result demonstrates that microarrays require only a very small quantity of carbohydrate; the loading of spot is 0.6 mL and therefore the minimum amount for the detection is attomol ($10^{-18}$ mole) per spot, allowing several experiments to be carried out on a single glass slide. Assay miniaturization through the construction of high density microarrays is thus well suited for the investigation of carbohydrate-protein interaction.

Multivalent Carbohydrate-Protein Interaction on Surface. FITC labeled Con A was incubated with different printing concentrations of Man1 on the surface, after washing the slide was scanned to get the fluorescence intensities. A binding curve based on printing concentrations and fluorescence intensities was created, and the binding curve reached saturation (in the case of FITC-Con A and Man1, the curve became saturated at 10 μM printing conc.), which was independent of surface density (surface saturated when printing conc. was over 100 μM). This saturated curve is an indication of multivalent interaction between protein and printed carbohydrates. As the signal intensity in an array depends on the surface density of the immobilized carbohydrate, it is essential to normalize carbohydrate concentrations prior to printing.

Figure 2A:
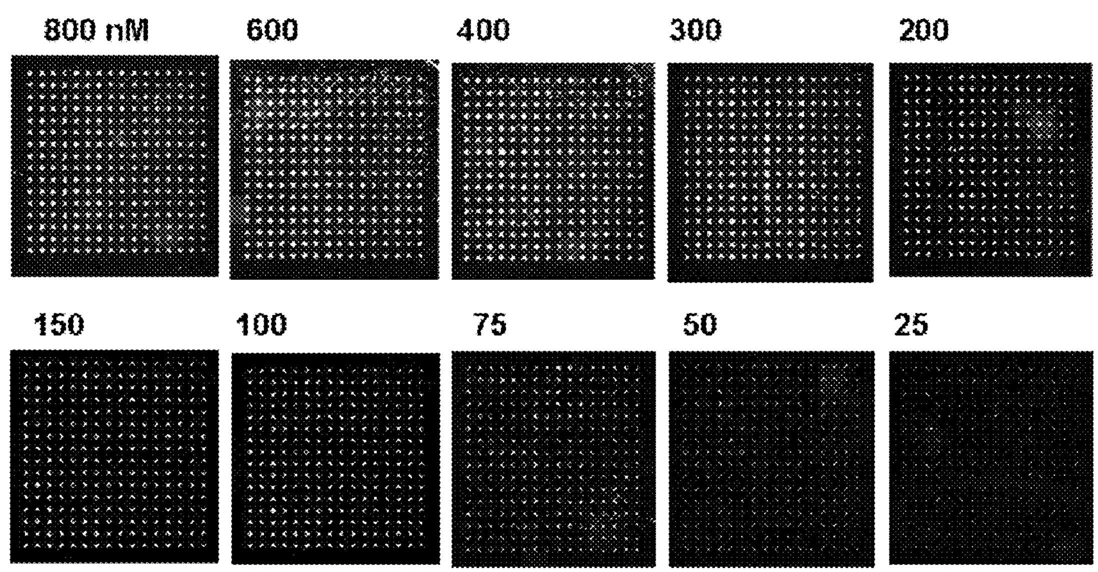
Figure 2B:
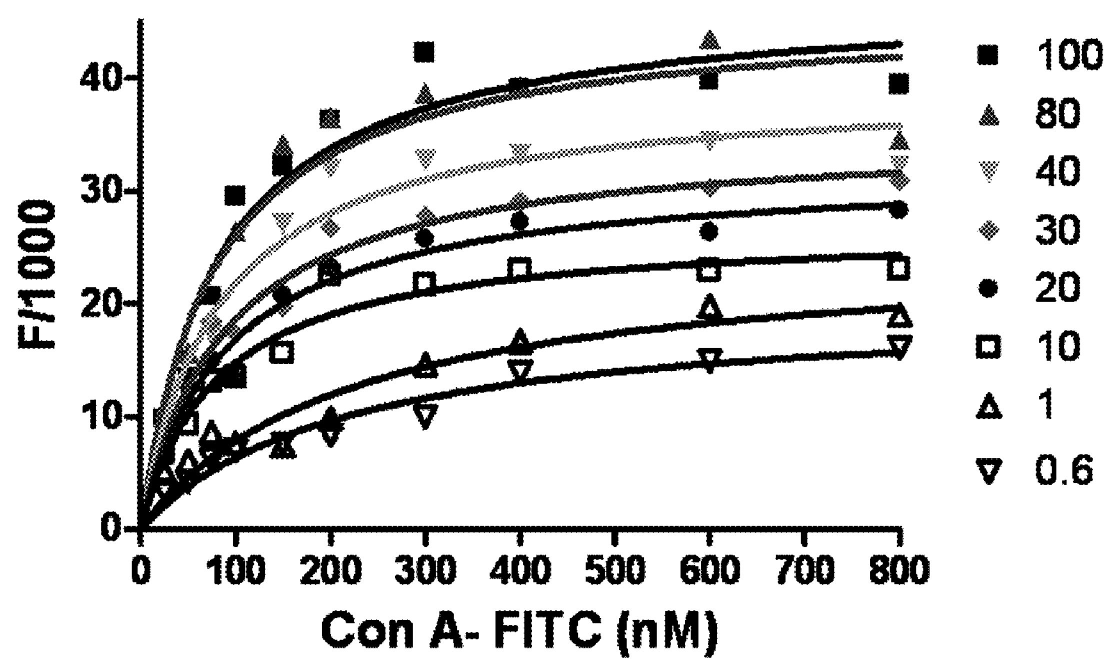

In order to determine the dissociation constant on surface, protein concentrations were plotted against fluorescence intensity at different concentrations of printed sugar. FIG. 2a depicts photographs of glass slides printed at 16 different concentrations with 16×16 pattern of Man1 from 100 μM (first left column) to 0.1 μM (first right column) The arrays were probed with ten concentrations of protein-FITC labeled Con A, ranging from 800 nM to 25 nM. Con A concentrations were plotted against median fluorescence intensities of replicate spots to give a set of curves (FIG. 2b). The curves were analyzed as Langmuir isotherms, assuming that the system reached equilibrium during incubation, $$F = \frac{F\max[P]}{[P] + K_{D,surf}} \tag{1}$$

where $F_{max}$ is the maximum fluorescence intensity, a measure of the amount of active carbohydrate on the surface; [P] is the total lectin concentration; and $K_D$, surf the equilibrium dissociation constant for surface carbohydrate and lectin. Although the printed concentrations of mono-mannose vary by up to 10-fold from 100 to 10 μM, the $K_{D,surf}$ values obtained from these individual curves, as well as from replicate experiments, are narrowly distributed (mean $K_D$,surface=83 nM; s.d.=4.7 nM; FIG. 9). However, at lower printing concentration (ca. 1 μM), the surface reaches a critical density, at which point the binding affinity is lower, probably due to the increased spatial separation (distance) between the carbohydrates on the surface. This is because Con A is capable of forming two attachment points to the surface and the distance between these points is approximately 65 Å. At the printing concentration of over 10 μM, the distance between mannose residues on the surface is close enough such that on average, an adsorbed Con A can bind to two mannose residues. However, when the printing concentration is below 10 mM, the average distance (spatial separation) between immobilized mannose residues is too far for a multivalent interaction with Con A.

FIG. 7 provides a diagrammatic overview of the impact of concentration on multivalent binding. Each black group of four circles represents a protein. The protein is representative of Con A which has 4 binding sites (each site is separated by a distance of about 6.5 nm). The light grey dots attached to the substrate are representative of sugar on the surface. When printing of the sugars is at low concentration the distance between any 2 sugars is represented in FIG. 7a. In FIG. 7a the distance between 2 binding sites is too far for the protein with multiple binding sites to interact with more than one sugar. FIG. 7b represents the sugars printed at a higher concentration, in this case sugars have a spatial separation which is close enough for the protein to interact with 2 sugars. (The $K_{D,surf}$ values indicated that for a printing conc<=1 μM, the $K_{D,surf}$ value increased and there was less tight binding), at this low concentration the average distance between 2 sugars (glycans) is about 10 nm.

Figure 3A:
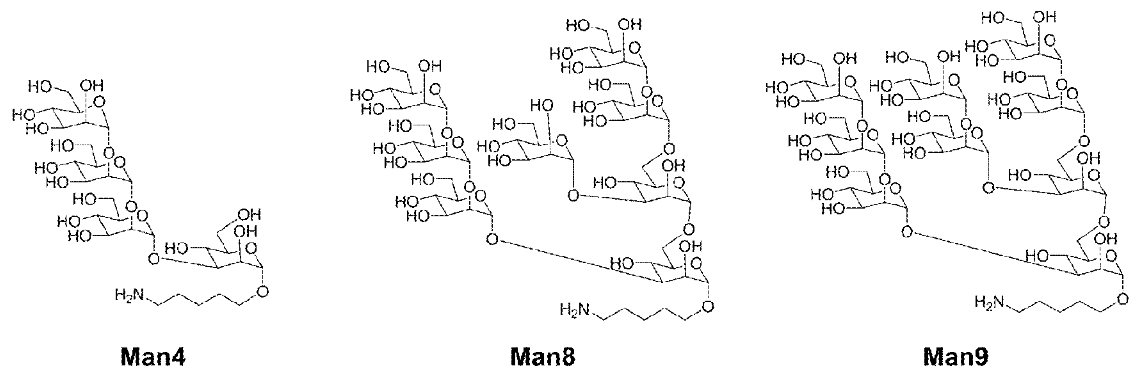
FIG. 3 shows implementations of (a) structures of Man4, Man8, Man9; and (b) the binding curves were obtained from the function of lectins or antibody concentration and fluorescence intensity determined from array images. $K_{D,surf}$ values obtained by fitting the curves to eq 1. The error bars indicated in the figures show the average percentage error for all data points reported in the figures.

The increase in binding strength for multivalent interactions is shown in the $K_{D,surf}$ values for high surface densities of a carbohydrate is the result of multivalent interactions. It is well known that carbohydrate-binding proteins interact weakly with monovalent ligands but strongly with multivalent carbohydrates. FITC washing-off experiment indicated that the average space between each sugar is about 100 Å at printing concentration of 1 μM. This result verifies FITC to be an appropriate model for the determination of sugar density. Accordingly, in some exemplary implementations is a method is disclosed to determine the distance of two binding sites within one protein. Applying at least some aspects of this method, different carbohydrates (Man1, Man4, Man8, Man9—see FIG. 3*a*) were printed at 100 μM and measured their binding to different proteins at different concentrations. The mannose binding lectins Con A, Lens culinaris agglutinin (LCA), Pisum sativum agglutinin (PSA), and the human monoclonal antibody-2G12 were each incubated with sugar arrays in different concentrations.

The increase in binding strength for multivalent interactions is shown in the $K_{D,surf}$ values for high surface densities of a carbohydrate is the result of multivalent interactions. It is well known that carbohydrate-binding proteins interact weakly with monovalent ligands but strongly with multivalent carbohydrates. FITC washing-off experiment indicated that the average space between each sugar is about 100 Å at printing concentration of 1 □M. This result verifies FITC to be an appropriate model for the determination of sugar density. Accordingly, in some exemplary implementations is a method is disclosed to determine the distance of two binding sites within one protein. Applying at least some aspects of this method, different carbohydrates (Man1, Man4, Man8, Man9—see FIG. 3*a*) were printed at 100 μM and measured their binding to different proteins at different concentrations. The mannose binding lectins Con A, *Lens culinaris* agglutinin (LCA), *Pisum sativum* agglutinin (PSA), and the human monoclonal antibody-2G12 were each incubated with sugar arrays in different concentrations.

Figure 3B:
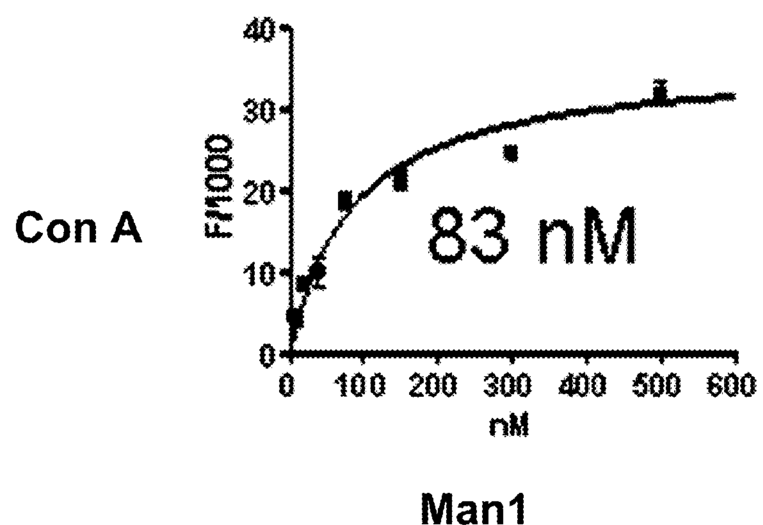
Figure 3B:
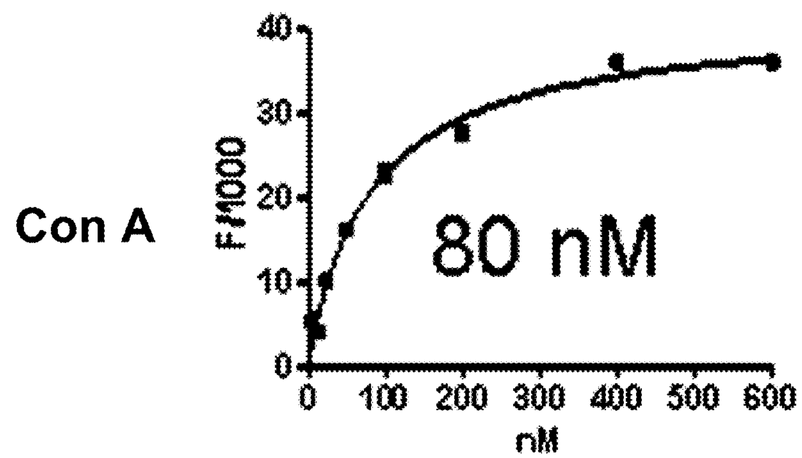
Figure 3B:
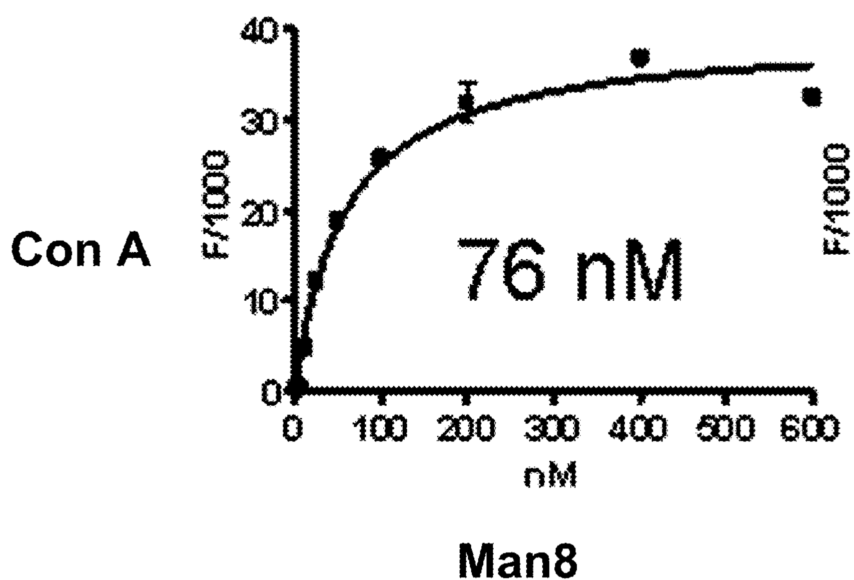
Figure 3B:
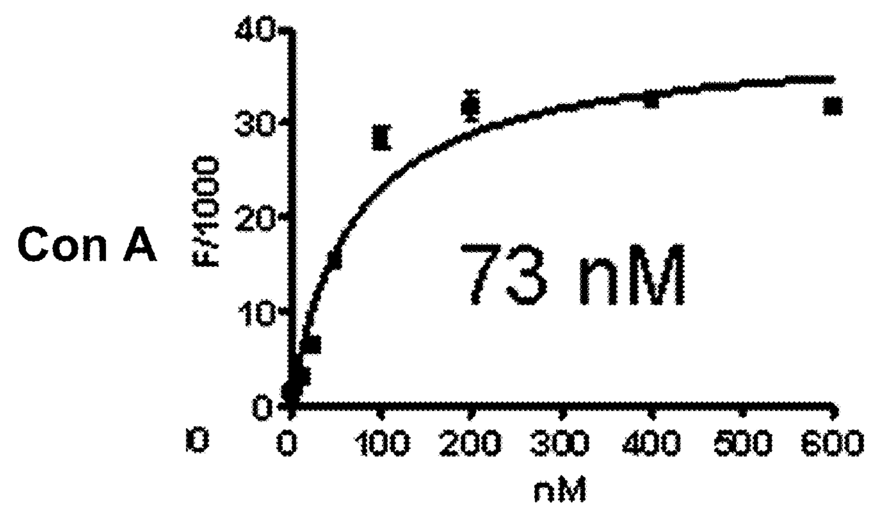
Figure 3B:
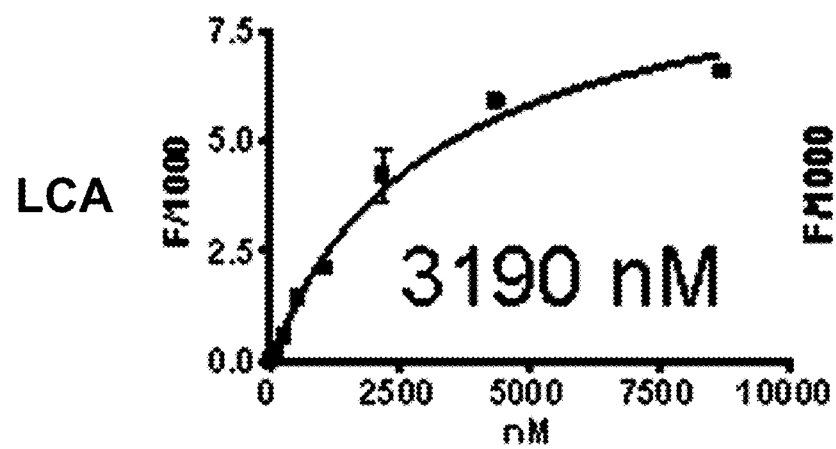
Figure 3B:
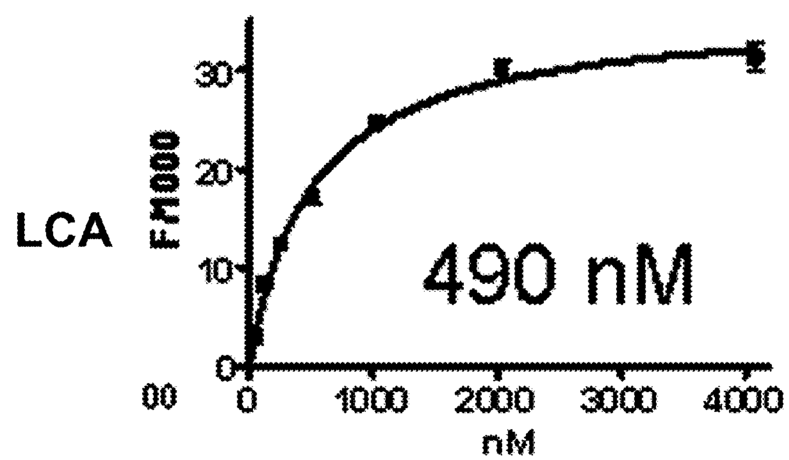
Figure 3B:
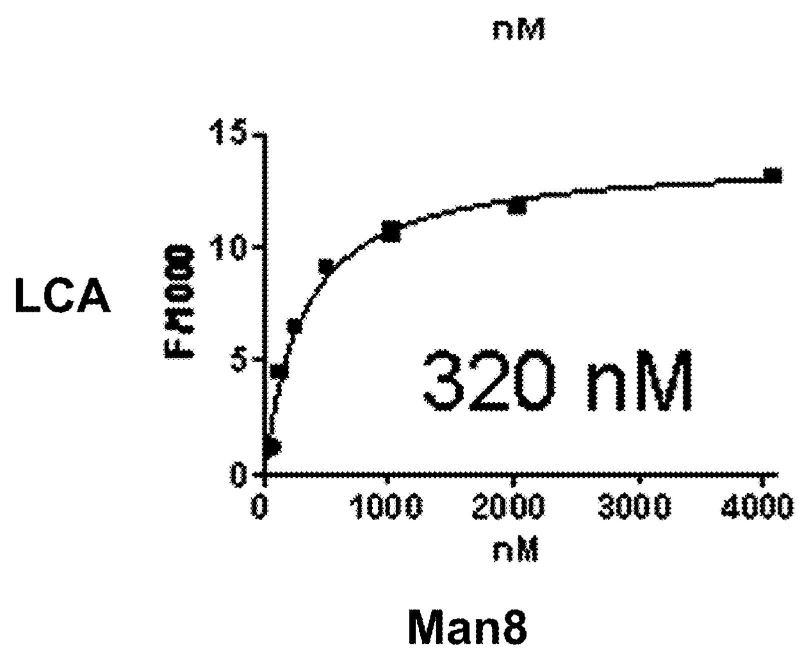
Figure 3B:
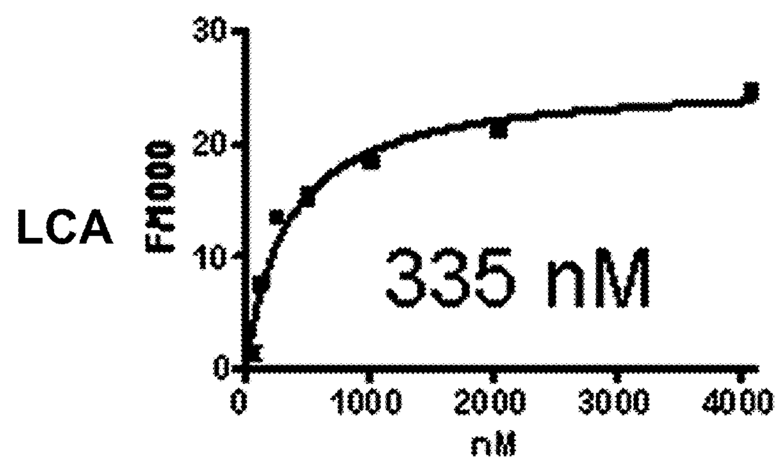
Figure 3B:
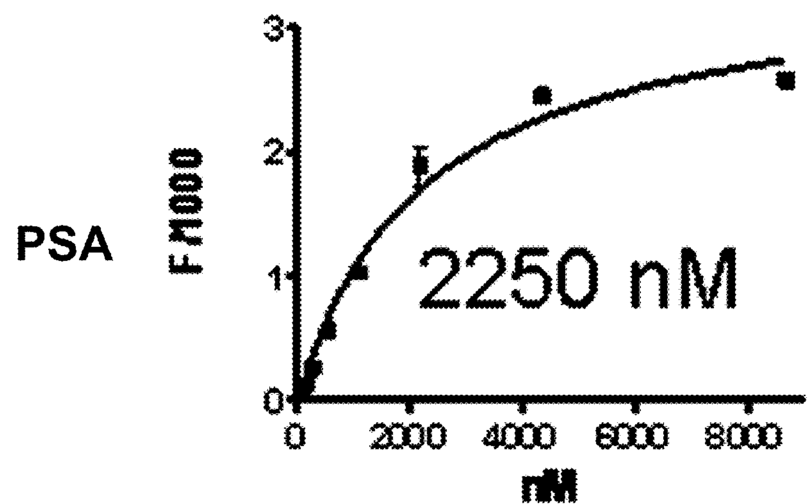
Figure 3B:
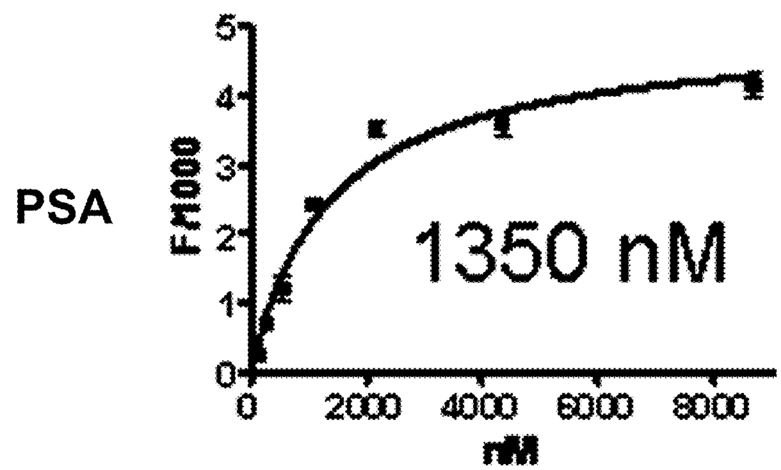
Figure 3B:
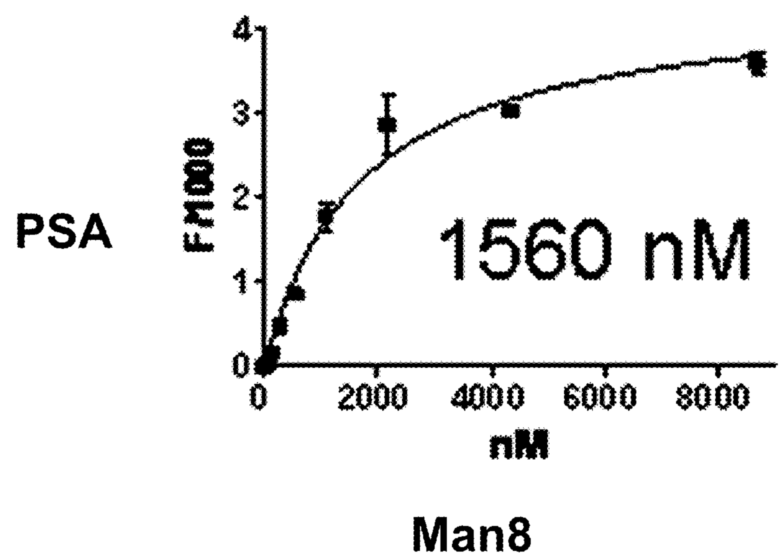
Figure 3B:
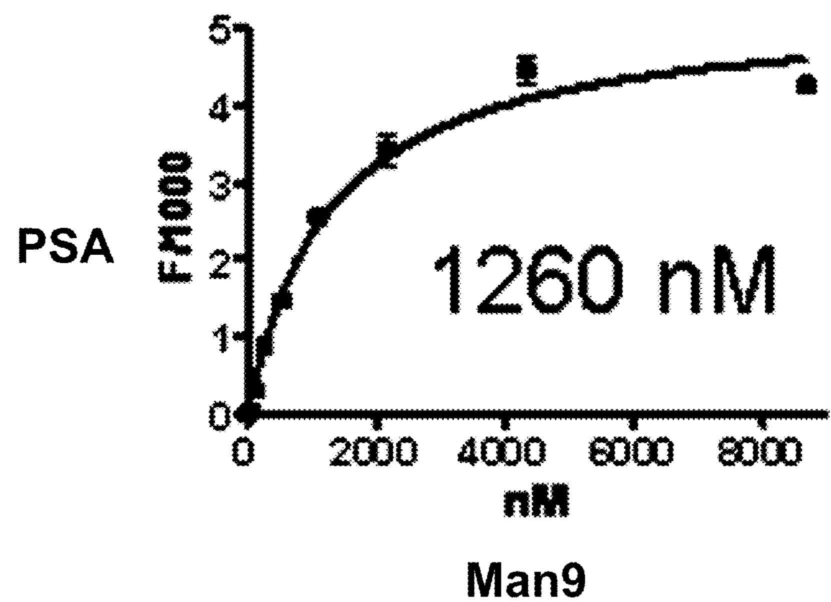
Figure 3B:
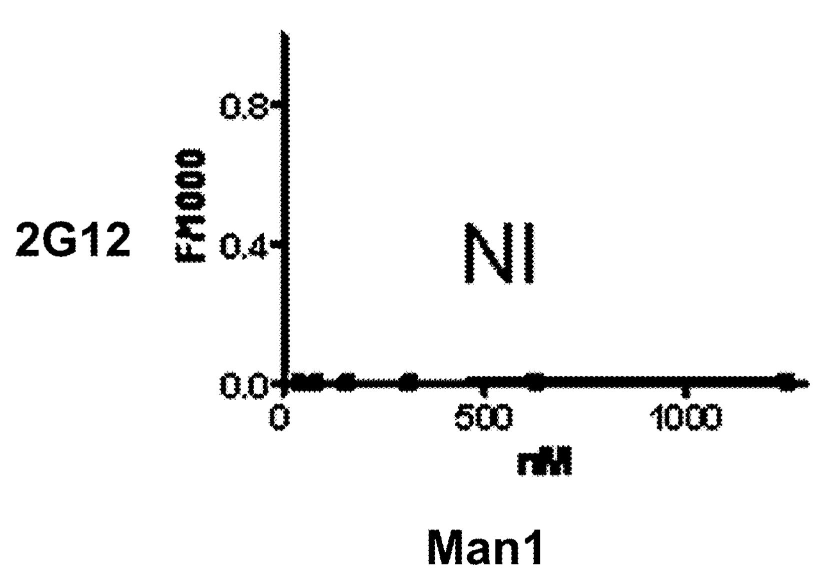
Figure 3B:
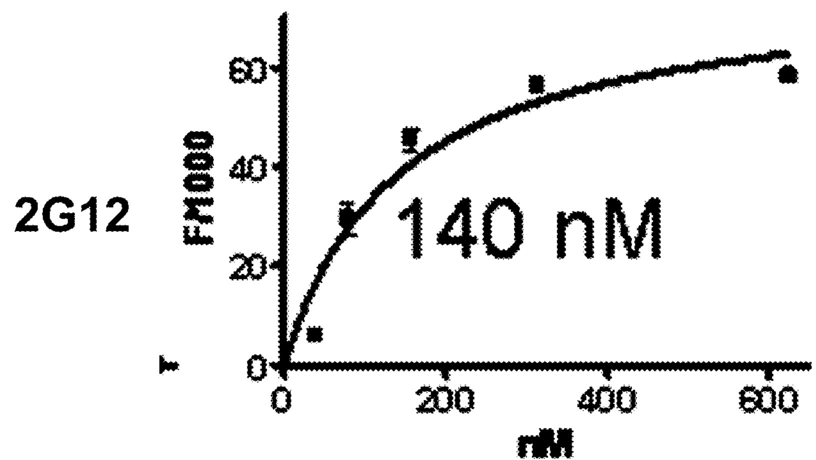
Figure 3B:
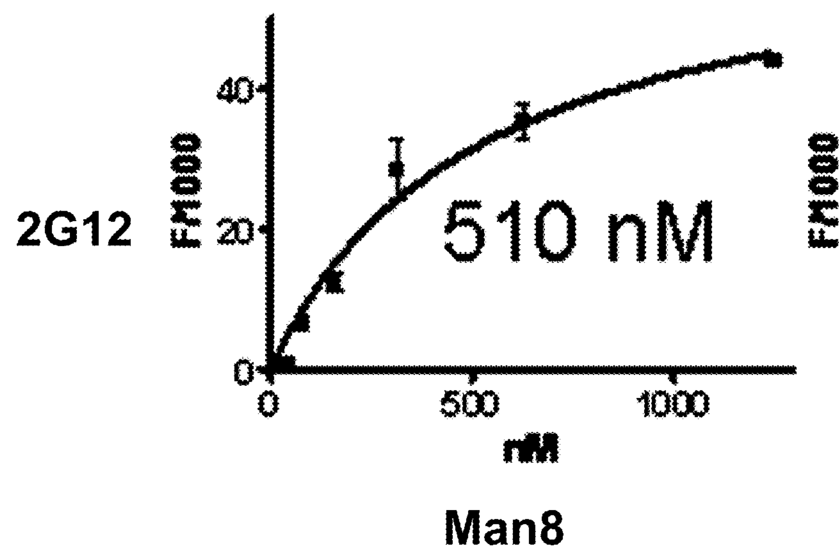
Figure 3B:
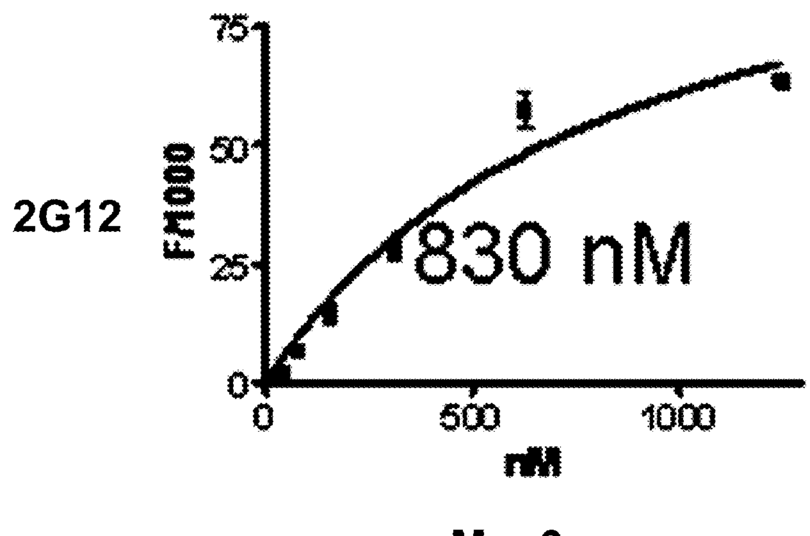

The model disclosed herein for binding fit the data well and $K_{D,surf}$ values were obtained using eq 1 (FIG. 3*b*). The relative binding affinities of these lectins to surface mannose were observed as Con A>LCA>PSA. The binding affinities of Con A to the four carbohydrates were however close, all about 80 nM and consistent with the values determined by SPR. The relative binding specificity of LCA was Man9≈Man8≈Man4>Man1 and this strongly supported that LCA preferentially binds to poly-mannose structure. The garden pea lectin PSA is thought to have the same binding specificity to LCA, but in this experiment it was found that the binding trend of PSA to these oligosaccharides was similar to Con A, albeit weaker (up to two orders of magnitude). The human monoclonal antibody 2G12 against the mannose epitope of gp120 on HIV was reported to be in favor of the Mana1-2 Man structure. From this study, Man1 has no interaction and Man4 displayed the strongest interaction with $K_D$ of 140 nM. These values were consistent with previous measurements from the microtiter plate assay.

We also compared the binding strength of lectins or antibodies to mannose derivatives at one or two concentrations of these proteins and obtained a ranking order for binding specificities. For example, the relative binding strength, based on maximal fluorescence intensities, is Man4 (Fmax=36070)>Man9 (Fmax=25780)>Man8 (Fmax=13940)>Man1 (Fmax=9458), but that based on dissociation constants is Man8 ($K_D$=320 nM)>Man9 ($K_D$=335 nM)>Man4 ($K_D$=490 nM)>Man1 ($K_D$=3190 nM). Prior studies of carbohydrate-protein interactions have used a threshold-based, one-step qualitative analysis i.e. interaction or non-interaction. The threshold varies from one carbohydrate to another and is based on how well the carbohydrate behaves in the assay. Even when closely related glycans are studied under ideal conditions, they vary with respect to the surface density of active carbohydrates. Since the intensity of a spot depends both on $K_{D,surf}$ (which results from binding affinity), and $F_{max}$ (which results from surface active carbohydrate density and protein binding), the information obtained by probing an array with a single concentration of analytes may not be accurate. This present disclosures show that quantitative measurements can be carried out to accurately study the nature of carbohydrate-protein interaction on a cell surface.

Solution Dissociation Constant.

Figure 4A:
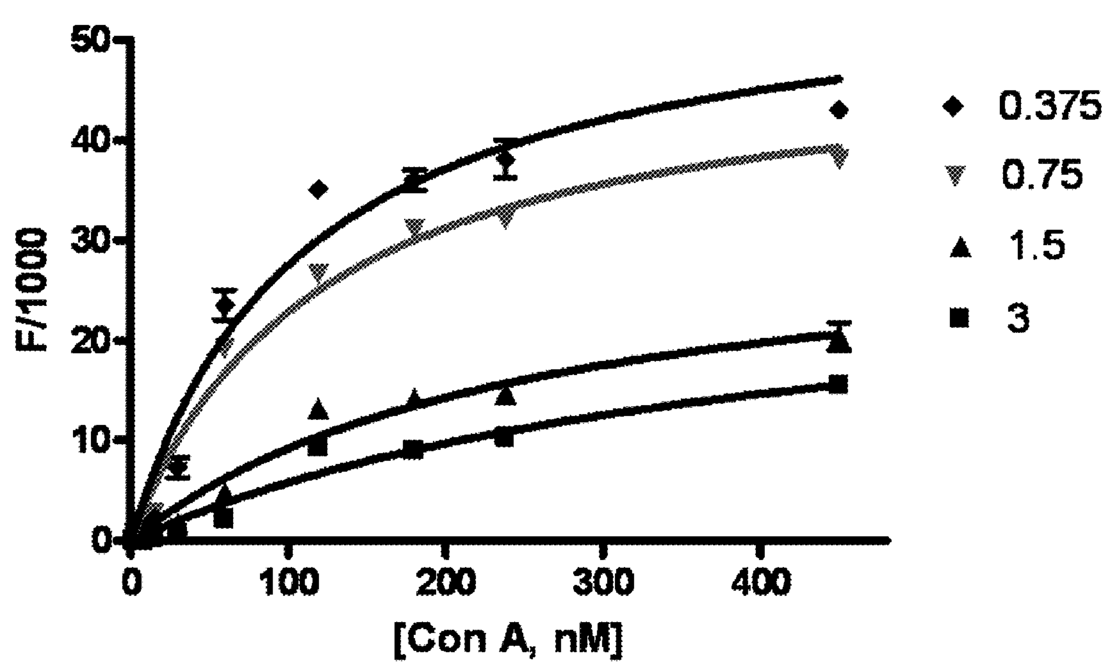
FIG. 4 shows implementations of (a) competition experiment between solution and surface Man8 for FITC-Man8. At different concentrations of the competitor, binding curves were obtained from the bound Con A concentrations and fluorescence intensities; and (b) the $K_D$ values were determined from a re-plot of the $K_{D\ app}$ versus free Man8 concentrations according to eq 2.
Figure 4B:
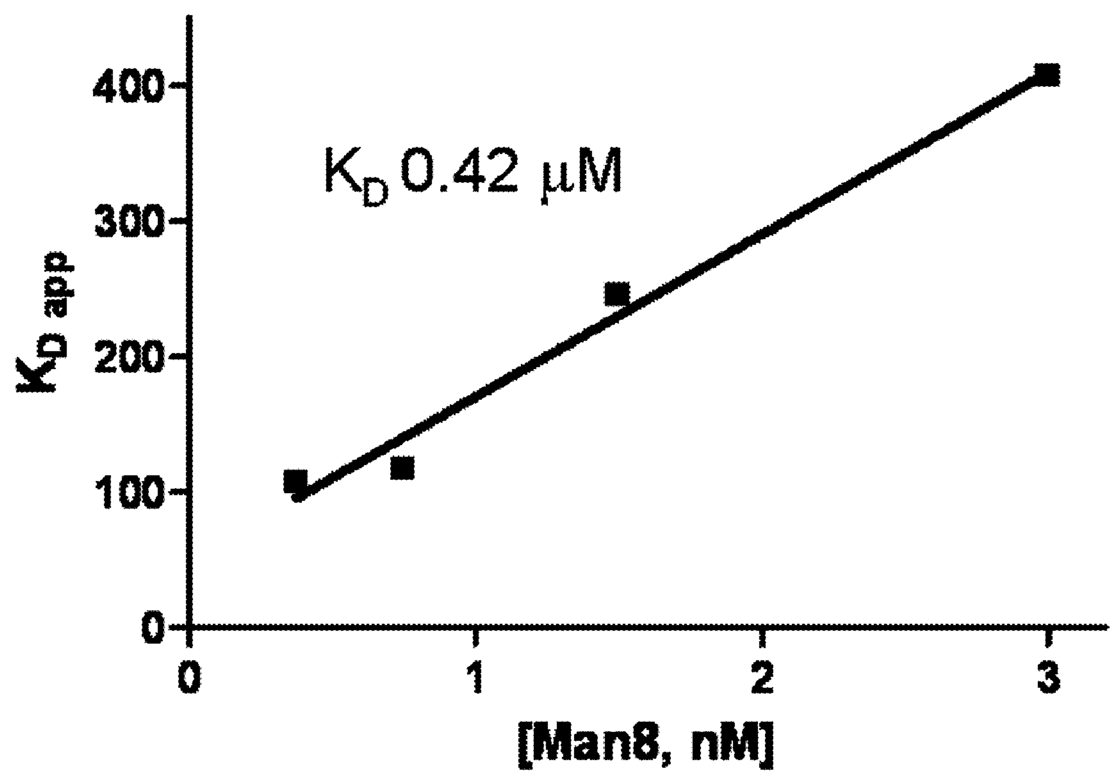

The solution equilibrium dissociation constant ($K_D$) for carbohydrate-lectin interactions can be determined using microarrays in a competitive assay. This analysis allows for the direct comparison between microarray affinities measurements to those obtained from solution-based affinity measurements. In a competitive binding experiment, carbohydrates in solution compete with immobilized carbohydrate ligands for the binding sites on the lectin, establishing a coupled equilibrium between the binding of protein to the immobilized species and to the species present in solution. Using array imaging signals, the unbound protein concentration [P] can be obtained via Langmuir isotherms (eq 1). Once the concentration of P has been measured, it is possible to determine the $K_D$ using eq 2, which is derived from the multivalent Scatchard formula (see the Experimental Section for the derivation of eq 2)

$$F = \frac{F\max[Po]}{[Po] + K_{D,surf}\left(1 + \frac{[Lo]}{K_D}\right)} \tag{2}$$

where [Lo] is ligand (carbohydrate) concentration applied to the system, and $K_D$ is the solution equilibrium dissociation constant. The derivation of this equation makes four assumptions: (1) the non-specific binding of protein to the slide surface is negligible compared to the total amount of protein in the system; (2) the binding sites in the protein bind to the ligand independently; (3) the initial concentration of ligand is much greater than the initial concentration of protein so that the concentration of unbound ligand is approximately equal to the total concentration of ligand (i.e., [Lo]≈[L]); and (4) the initial protein concentration for the system is greater than the initial concentration of protein-ligand complex (i.e., [Po]≈[P]). A competition binding experiment was performed by treating Con A to various oligomannoses, followed by incubation with corresponding oligomannoses surface. Binding curves, representing different concentrations of competitors were obtained as the function of FITC-Con A concentrations and fluorescence intensities from the Man8 surface (FIG. 4*a*). The data was analyzed according to eq 2, to afford apparent $K_D$ values, which were then replotted against competitor concentration to afford the solution $K_D$ values (FIG. 4*b*). Using this analysis, the $K_D$ values for Man1, Man4, Man8, Man9 for Con A were found to be 250 μM, 55 μM, 0.42 μM, and 0.13 μM, respectively. These values agree well with the solution dissociation constants of 0.3~1.0 mM for either Man8 or Man9 derivatives obtained from SPR followed by HPLC analysis. This analysis clearly shows that Man9 is more than $10^3$ fold stronger than Man1 in binding to Con A. This is because Man8 and Man9 are bivalent ligands containing the α(1,6) and α(1,3) arms of the core residue; where the α(1,6) was identified as the high affinity or primary site and α(1,3) arm as the low affinity or secondary site. A comparison of the solution $K_D$ (ex. 250 μM for the monovalent Man1) and the $K_{D,\ surf}$ (83 nM) values provide the extent of multivalent effect.

Competitive Inhibitors of carbohydrate-Binding Proteins in Solution.

Figure 5:
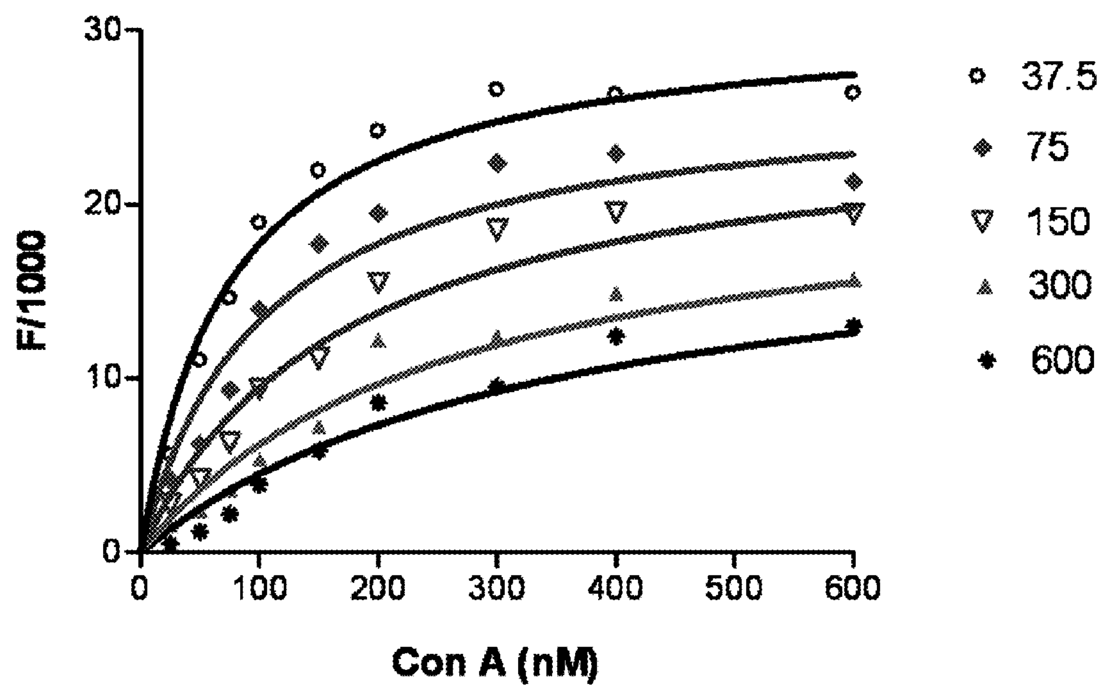
FIG. 5 shows binding curves obtained from implementations of the bound Man1-Con A concentrations and fluorescence intensities. Different curves mean different concentrations of competitor ((α-methyl)-mannosein the solution.

When different inhibitors (such as α-methyl mannose (a-MeMan), α-methyl glucose (a-MeGlc), and etc.) are applied to the system, binding curves can be analyzed using eq 10 and the inhibition constant $K_i$ can be obtained. Different concentrations of inhibitors were incubated with the slide bound with a protein of interest (FIG. 5), the fluorescent intensities were monitored, and then the $K_i$ values were determined (FIG. 10). The values agree well with the $K_i$ of 92 μM and 290 mM (for a-MeMan and a-MeGlc, respectively) obtained by SPR,[12] and with the $K_i$ of 120 μM and 520 μM (for a-MeMan and a-MeGlc, respectively) obtained by microcalorimetry measurements. The relative affinity value of a-MeMan to a-MeGlc ($K_D$ (a-MeGlc)/$K_D$ (a-MeMan)=4.3) is consistent with the result obtained from microcalorimetry measurements and dextran precipitation induced by Con A. These results indicate that this competition assay can reproduce the binding constants determined by well-tested solution methods. In addition, this method has an advantage in that only one surface is needed to rapidly measure a variety of inhibitors. Moreover, the microarray competition assay can illuminate the molecular features important for carbohydrate-protein complexation and will provide a basis for optimizing inhibitor structure.

The glycan array system described here offers several features that make it attractive as a tool for glycomics: it requires small quantities of materials ($10^{-18}$ mole) for high-throughput analysis, and can be used for quantitative analysis of carbohydrate-protein interaction on surface and in solution. The disclosed system is considered to be a good mimic of cell-surface arrays of carbohydrates in which the dissociation constants of multivalent interactions can be determined for comparison with the monovalent, solution dissociation constants determined through the competition analysis.

Example 1

Materials

NHS-coated glass slides (Nexterion H slide, SCHOTT North America; high density amine binding slide, Amersham bioscience), FITC labeled Concanavalin A (Con A, Sigma), FITC labeled *Lens culinaris* agglutinin (LCA, Sigma) and FITC labeled *Pisum sativum* agglutinin (PSA, Sigma), α-methyl mannose (Vector laboratory), α-methyl glucose (Acrose), α-methyl galactose (Sigma). Mannose derivatives (Man1, Man4, Man8, Man9) were synthesized as previously described.[35] Other standard chemicals were purchased from commercial suppliers, and used as received.

Example 2

Microarray Fabrication. Microarrays were printed (Genomic Solutions, Gene Machine) by robotic pin (SMP2B, TeleChem International Inc.) deposition of ~0.6 mL of various concentrations of amine-containing glycans in print buffer (300 mM phosphate, pH 8.5 containing 0.005% Tween-20) from a 384 well plate onto slides. The slide for (1) the scope of printing concentration studies: NHS-coated glass slides were printed with Man1 and FITC at 30 concentrations between 0.5 fM to 100 mM from left to right with 16 replicates vertically placed in each sub-array. Ten identical sub-arrays were fabricated in a 5×2 pattern and each sub-array consisted of a 30×16 pattern of spots, with a 0.25 mm pitch. After 1 h reaction, the slides surface was divided by drawing with permanent marker to avoid contamination for later protein incubation; (2) the slide for FIG. 2 was printed with Man1 with concentrations of 100 (first left column), 80, 60, 40, 30, 20, 10, 8, 6, 4, 2, 1, 0.8, 0.6, 0.4, and 0.1 mM (first right column, 16 different conc.) from left to right with 16 replicates vertically placed in each grid and totally 24 replicates (8×3 pattern) sub-arrays in one slide; (3) the slides for $K_{D,surf}$ and $K_D$ determination: the slides were printed of Man1, Man4, Man8, Man9 with concentration of 100 μM from right to left 16 replicates vertically placed in each grid and totally 24 sub-arrays replicates in one slide. After 1 day reaction, the slides were washed with PBST buffer (0.05% Tween 20) for 30 min and then blocked with blocking solution (super-block blocking buffer in PBS, Pierce) for another 1 hour. The slides were dried by purging with Ar gas and then stored at room temperature in a desiccator. The slides were washed with PBS buffer (pH 7.4) before use.

Example 3

Fluorescence wash-off measurements. FITC cadaverine (FIG. 6*a*) with concentration from 100 mM to 1 fM were printed onto the slide in 16 replicates and read at A488 by array scanner (Applied Precision). After 12 hr reaction at dark, the slide was washed with PBST (0.05% Tween 20) buffer. The slide was dried, and then read again at A488 by array reader (FIG. 6*b*). The average intensity from each concentration was plotted (FIG. 6*c*). The curve showed that at concentrations below 100 μM, the fraction of surface covered by each molecule varied in proportion to its concentration (FIG. 6*d*). Over 500 μM, the surface seems to be saturated (FIG. 6*c*). The number of FITC that remain bound to the surface (Np) is calculated by eq 3.

$$Np = \frac{CVN_A Qpost}{Qpre} \quad (3)$$

Since the printing concentration, C=500 μM or 100 μM, and the volume, V=0.6 nL, $N_A$ is Avogadro's Number. Each spot in the array is around 0.1 mm diameter.

When the surface is saturated (around 100 mM to 500 mM printing FITC), the ratio from pre-quench (Qpre) to post-quench (Qpost) is 0.23 (obtained from the array scanner measurement before and after washing). Based on equation 3, the surface density is between $1.8\times10^{14}$ molecules/cm$^2$ and $8.8\times10^{14}$ molecules/cm$^2$. When the printing concentration at 1 mM, the ratio of Qpost/Qpre is 0.1, the density is $0.77\times10^{12}$ molecules/cm$^2$. If the surface was assumed to be of a homogenous distribution, the average space between each molecule is $115\times10^{-8}$ m (115 Å).

Example 4

Direct Binding Assay

FITC-labeled Con A (4 mg/mL), FITC-labeled PSA (2 mg/ml), FITC-labeled LCA (2 mg/ml), were diluted in PBS-BSA buffer (50 mM, pH 6.5; 1 mM $CaCl_2$, 1 mM MnCl, 0.9% NaCl (w/v), 1% BSA (w/v)). Human monoclonal antibody-2G12 was used in PBST buffer with 1% BSA. For all incubations, 10-25 μL of protein solution was applied to each sub-array using a 24 well bottomless incubation chamber (The Gel Company). Humidifying incubation was performed under foil and using a shaker for 1 h at room temperature. The slide was washed three times with incubation buffer, three times with PBST buffer (0.05% Tween-20), three times with distilled water, and then centrifuged at 200 g for 5 min to ensure complete dryness. The array was then imaged at a resolution of 5 Åm with a A488 laser using ArrayWorx microarray reader to visualize fluorescence. The method for the interaction of human monoclonal antibody-2G12 with sugars was similar to lectin. 2G12 in PBST buffer with 1% BSA was pre-complex with Cy3 labeled goat anti-human IgG (Jackson ImmunoResearch) and then placed to the slide and incubated for 1 h. The images were read using A595 laser with the array reader.

Example 5

Competitive Binding Assay

15 μl of series dilutions of competitor was incubated with different concentrations of protein (15 μl). The mixture was then loaded onto the slides by using a 24 well incubation chamber and incubated for 1 h under a humidifying container at room temperature. The following procedure is the same as the direct binding assay.

Example 6

Data Analysis

ArrayVision 8.0 (Applied Precision) was used for the fluorescence analysis and extraction of data. Equilibrium binding data were analyzed by fitting the data to the appropriate equation, assuming that ligands bound to one or two independent sites, using the commercial non-linear regression program GrapPad PRISM (GraphPad). The error bars indicated in the figures show the average percentage error for all data points reported in the figures.

Example 7

Calculation

The formation of surface-bound complex (LP) on the slide between analyte protein (P) and surface bound ligand (L) can be generally considered to the simple bimolecular reversible reaction scheme.[43]

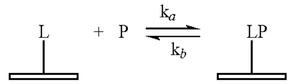

The observed rate of complex formation may be written $$\frac{d[LP]}{dt} = K_a[L][P] - K_b[LP] \quad (4)$$

The concentration of unoccupied ligand [L] is the difference between the total amount of ligand [Lo] and the amount of [LP]. Substituting [Lo]−[LP] for [L] in eq 4 gives $$\frac{d[LP]}{dt} = K_a[P]([Lo] - [LP]) - K_b[LP] \quad (5)$$

if the total amount of ligand [Lo] is expressed in terms of maximum analyte binding capacity of the surface, all concentration terms can then be expressed a binding signal response (F).

$$\frac{d[F]}{dt} = K_a[P](F\max - F) - K_bF \quad (6)$$

When at equilibrium d[F]/dt=0 and $K_{D,surf}=k_d/k_a$ the dissociation constant of ligand and protein complex is obtained as shown in eq 1.

The interaction between a monovalent ligand (L) in the solution, a monovalent ligand (L) on the surface, and a multivalent protein (P) can be represented as

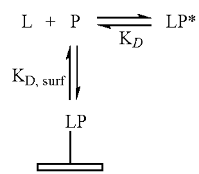

The expression for the equilibrium solution dissociation constant for this interaction is $$K_D = \frac{[L][P]}{[LP^*]} \quad (7)$$

where [LP*] is the concentration of protein/ligand complexes, [P] is the concentration of free protein, and [L] is the concentration of free ligand. Since a multivalent protein (P) may have q binding sites (B), the concentration of free binding sites [B] is equal to q[P]. Likewise, the formation of a binding site/ligand complex [BP*] is equal to q[LP*]. From the eq 7, both numerator and denominator multiply q value. The interaction of one acceptor binding site with ligand can be represented as $$K_D = \frac{q[L][P]}{q[LP^*]} = \frac{[L][B]}{[LB^*]} \quad (8)$$

Since the binding sites in the protein bind to the ligands independently, the individual dissociation constant is therefore the same as protein dissociation constant.

Then, a value is defined as ratio of free protein and total protein which is then substituted [LP*] value by eq 7 and rearranged to give eq 9.

$$\alpha = \frac{[P]}{[P] + [LP^*]} = \frac{1}{\frac{[Lo]}{K_D} + 1} \quad (9)$$

To determine $K_D$, the unbound protein in this system is calculated to become a[Po] and which is substituted to eq 1 and rearranges to yield eq 2.

The interaction between inhibitors (I) in the solution, a ligand (L) on the surface, and a multivalent protein (P) can be represented as

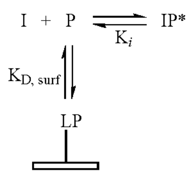

The array imaging data is used to measure [P] and $K_i$ can be determined by the eq 10.

$$F = \frac{F\max[Po]}{[Po] + K_{D,surf}\left(1 + \frac{[I]}{K_i}\right)} \tag{10}$$

The fraction of inhibition (f) is equal to 1−F/Fmax, the equation from eq 10 can be rearranged to give eq 11.

$$1 - \frac{F}{F\max} = f = \frac{[I]}{[I] + K_i\left(1 + \frac{[Po]}{K_D}\right)} \tag{11}$$

Shown in FIG. 8 is an exemplar of a method and process of a sugar fixed to the surface of an array substrate interacting with different concentrations of lectin (which a florescence attached). To obtain the surface KD value different concentration of inhibitors (shown as light grey connected hexagons) were added to the microarray, each concentration of inhibitor can generate an isotherm (right bottom chart.). Based on the isotherms the solution KD or Ki for the inhibitors may be obtained.

While the method and agent have been described in terms of what are presently considered to be the most practical and preferred implementations, it is to be understood that the disclosure need not be limited to the disclosed exemplary implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

The invention claimed is:

1. A high-throughput method of identifying a protein bound to a microarray of attomol quantity carbohydrates, the method comprising:

forming a glycan microarray of spotted sugars in concentrations each of about $10^{-18}$ moles per spot, wherein each spot consists of a polymeric sugar structure;

adding a labeled protein to the microarray;

incubating the microarray; and using an array reader to identify labeled proteins on the glycan microarray.

2. The method of claim 1, further comprising calculating the binding affinity between the labeled proteins and the spotted sugars.

3. The method of claim 1, further comprising calculating the surface disassociation constant of the proteins and the spotted sugars.

* * * * *